United States Patent
Yada et al.

(10) Patent No.: US 7,868,202 B2
(45) Date of Patent: Jan. 11, 2011

(54) PROCESS FOR PRODUCING (METH)ACROLEIN OR (METH)ACRYLIC ACID

(75) Inventors: Shuhei Yada, Mie (JP); Hiroki Kawahara, Mie (JP); Yukihiro Hasegawa, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 318 days.

(21) Appl. No.: 11/597,276

(22) PCT Filed: Dec. 13, 2004

(86) PCT No.: PCT/JP2004/018561
§ 371 (c)(1), (2), (4) Date: Aug. 20, 2007

(87) PCT Pub. No.: WO2005/110960
PCT Pub. Date: Nov. 24, 2005

(65) Prior Publication Data
US 2008/0071109 A1    Mar. 20, 2008

(30) Foreign Application Priority Data
May 19, 2004    (JP)    ............... 2004-148875

(51) Int. Cl.
C07C 51/16    (2006.01)
(52) U.S. Cl. ............................ 562/544; 562/549
(58) Field of Classification Search .................. None
See application file for complete search history.

(56) References Cited
U.S. PATENT DOCUMENTS 5,188,376 A * 2/1993 Ueda et al. ............ 277/536
5,518,027 A * 5/1996 Saiki et al. ............ 137/550
7,011,312 B2 * 3/2006 Ishida .................... 277/342
7,052,657 B2 * 5/2006 Nakajima et al. ...... 422/198

(Continued)

FOREIGN PATENT DOCUMENTS

EP    1 080 781 A1    3/2001

(Continued)

OTHER PUBLICATIONS

U.S. Appl. No. 11/597,365, filed Nov. 22, 2006, Ogawa, et al.

(Continued)

*Primary Examiner*—Karl J Puttlitz
(74) *Attorney, Agent, or Firm*—Oblon, Spivak, McClelland, Maier & Neustadt, L.L.P.

(57) ABSTRACT

The object of the invention is to provide a method for producing (meth)acrolein or (meth)acrylic acid by gas phase catalytic oxidation reaction, which can perform smooth temperature control of the heat medium, can prevent hot spot effectively and can be handled easily, and an apparatus.

The invention are a method for producing (meth)acrolein or (meth)acrylic acid by carrying out gas phase catalytic oxidation reaction of propane, propylene, isobutylene or (meth)acrolein with an oxygen-containing gas using an inorganic salt as a reaction temperature adjusting heat medium, characterized in that the material of a gland packing member which seals body part of a regulating valve arranged on a heat medium feeder and controlling supply and circulation velocity of the heat medium and a rotation axis that interfits to the body part, in such a manner that they can perform sliding, is a mica-based material, and a production apparatus.

11 Claims, 4 Drawing Sheets

U.S. PATENT DOCUMENTS

| | | | |
|---|---|---|---|
| 7,270,875 B2 * | 9/2007 | Ishida et al. | 428/324 |
| 2003/0079857 A1 | 5/2003 | Mori et al. | |
| 2003/0080308 A1 * | 5/2003 | Gonsior | 251/214 |

FOREIGN PATENT DOCUMENTS

| | | | |
|---|---|---|---|
| EP | 1080781 | * | 3/2001 |
| EP | 1 271 122 A2 | | 1/2003 |
| JP | 48-15561 | | 2/1973 |
| JP | 61-24589 | | 6/1986 |
| JP | 6-249345 | | 9/1994 |
| JP | 8-92147 | | 4/1996 |
| JP | 2001192644 | * | 7/2001 |
| JP | 2002-340187 | | 11/2002 |
| JP | 2003-83833 | | 3/2003 |
| JP | 2003-321404 | | 11/2003 |
| JP | 2004-944 | | 1/2004 |
| JP | 2004-51902 | | 2/2004 |

OTHER PUBLICATIONS

U.S. Appl. No. 11/596,366, filed Nov. 14, 2006, Ogawa, et al.
U.S. Appl. No. 11/596,287, filed Nov. 13, 2006, Jinno, et al.
U.S. Appl. No. 11/587,990, filed Oct. 30, 2006, Jinno, et al.
U.S. Appl. No. 11/547,864, filed Oct. 6, 2006, Ogawa, et al.
U.S. Appl. No. 11/451,355, filed Jun. 13, 2006, Yada, et al.
"Valqua Seals Handbook", Nippon Valqua Industries Ltd., Aug. 20, 1978, 5 pages, (with partial English translation and Concise Explanation).

* cited by examiner

PROCESS FOR PRODUCING (METH)ACROLEIN OR (METH)ACRYLIC ACID

TECHNICAL FIELD

This invention relates to a method for producing (meth)acrolein or (meth)acrylic acid. More particularly, it relates to a production method by a process in which (meth)acrolein or (meth)acrylic acid is efficiently produced by carrying out gas phase catalytic oxidation of propylene, propane or isobutylene using molecular oxygen.

BACKGROUND ART (Meth)acrolein or (meth)acrylic acid and is generally produced by a gas phase catalytic oxidation reaction of propylene, propane or isobutylene using a multi-tubular reactor and using molecular oxygen or a molecular oxygen-containing gas in the presence of a composite oxide catalyst.

Patent Reference 1 (JP-A-8-92147) discloses a method in which temperature of a fluid for removing heat (to be referred to as "heat medium" hereinafter) is equalized by controlling a temperature difference in a reactor from its inlet to outlet at from 2 to 10° C. or less, by effecting parallel flow of the flow of the heat medium in the reactor shell with the flow direction of a reaction gas fed into the reactor and also effecting meandering ascent of flow of the heat medium using baffles.

Proposals are extremely scarce regarding equipment for controlling reaction temperature, for the purpose of industrially controlling the reaction having a large calorific value.

Patent Reference 1: JP-A-8-92147

DISCLOSURE OF THE INVENTION

Problems that the Invention is to Solve

The object of the invention is to propose an apparatus capable of controlling excellent reaction temperature, which is a basis for stable operating a gas phase catalytic oxidation method without deactivating catalyst of a reactor, and a method for producing (meth)acrolein or (meth)acrylic acid using the same.

The multi-tubular reactor generally used in the gas phase catalytic oxidation method is a method for obtaining an oxidized product by an oxidation reaction in which a solid catalyst is filled therein and allowed to contact with a raw material.

Since a large number of tubes (a bundle of tubes) are vertically arranged in the multi-tubular reactor in general, the process fluid side can be up-flowed or down-flowed by feeding a process fluid from the upper side or lower side. The heat medium can also be supplied to the reactor shell side from the upper side or lower side. That is, 1) a parallel flow system of process fluid side down flow/heat medium down flow, 2) a parallel flow system of process fluid side up flow/heat medium up flow, 3) a counter flow system of process fluid side up flow/heat medium down flow and 4) a counter flow system of process fluid side down flow/heat medium up flow can be considered.

In such a multi-tubular reactor, a temperature necessary for the reaction is maintained by circulating a temperature-controlled heat medium around the out side of its reaction tube bundle (shell side), and at the same time, a method is introduced in which deterioration or inactivation of a catalyst in tubes due to excess increase of the process fluid temperature (formation of hot spot (active spot)) is prevented by simultaneously carrying out heat exchange between the process fluid (a process gas in the case of the gas phase catalytic oxidation reaction) and the heat medium, like the case of a heat exchanger frequently used in chemical plants.

However, when produced by carrying out gas phase catalytic oxidation reaction of propylene, propane or isobutylene using molecular oxygen or a molecular oxygen-containing gas in the presence of a composite oxide catalyst, heat of reaction of the gas phase catalytic oxidation reaction is so high that there are many cases of causing problems due to insufficient temperature control in the conventionally known many conceived devices even when a minutely designed catalyst is used, such as deterioration of the catalyst due to too increased temperature of a specific position of the catalyst layer, a run away reaction caused by exceeding acceptable temperature of the catalyst, or the catalyst becomes unserviceable.

One of the causes is that the heat medium temperature outside of the reaction tube bundle (shell side), which is a basis of the industrial equipment, cannot be set to a predetermined value.

It is generally carried out that a heat medium having increased temperature due to absorption of heat of reaction is cooled and set to a predetermined temperature and then again circulated into the reactor, but in the case of a raw material of (meth)acrolein or (meth)acrylic acid and molecular oxygen or a molecular oxygen-containing gas, it is general, for preventing the aforementioned run away reaction on the catalyst layer, that this circulation is carried out by selecting kind and amount of the heat medium such that its calorific capacity becomes extremely large, thereby controlling the temperature difference between the reactor inlet and the outlet (after endothermic step of heat of reaction) at a level of from 1 to 3° C.

A heat exchanger is generally used for the purpose of correcting such a small temperature difference of a large amount of the heat medium, and a nitrate mixture (niter) is frequently used as the heat medium to be used due to the temperature condition, but since the niter has a high melting point and therefore is easily solidified, it induces operation failure of a valve to be used in the temperature control, so that delicate temperature control becomes difficult and (in spite of the precious designing of the catalyst and reactor structure which can prevent run away reaction) run away reaction is induced in some cases.

The invention has been made by taking the aforementioned actual circumstances into consideration, and its object is to provide a method for producing (meth)acrolein or (meth)acrylic acid by carrying out gas phase catalytic oxidation reaction of a raw material of (meth)acrolein or (meth)acrylic acid with molecular oxygen or a molecular oxygen-containing gas, which is an industrial production method in which the product of interest can be stably produced while maintaining its quality, by carrying out temperature control of the heat medium smoothly and with good accuracy and thereby effectively preventing formation of hot spot (active spot), and a production apparatus thereof.

The present inventors have found a method which supports a method in which a heat medium to be used in an oxidation reactor for producing (meth)acrylic acid or the like can exclude operation failure of a valve arranged on the piping to be used, and thereby facilitating temperature control of the heat medium or handling of the medium and preventing various run away reactions.

Means for Solving the Problems

The object of the invention has been accomplished by the following means.

(1) A method for producing (meth)acrolein or (meth)acrylic acid by carrying out gas phase catalytic oxidation reaction of propane, propylene, isobutylene or (meth)acrolein with an oxygen-containing gas using an inorganic salt as a reaction temperature adjusting heat medium, characterized in that the material of a gland packing member which seals body part of a regulating valve arranged on a heat medium feeder and controlling supply and circulation velocity of the heat medium and a rotation axis that interfits to the body part, in such a manner that they can perform sliding, is a mica-based material.

(2) The method for producing (meth)acrolein or (meth)acrylic acid according to the aforementioned (1), wherein gland part of the aforementioned regulating valve has a structure of having a heating jacket.

(3) The method for producing (meth)acrolein or (meth)acrylic acid according to the aforementioned (1) or (2), wherein actuator of the aforementioned regulating valve has a [sliding frictional force between the body part and a stem interfitting thereto]/[actuator maximum generation force] value of 0.2 or less in the state of not flowing a fluid.

(4) The method for producing (meth)acrolein or (meth)acrylic acid according to the aforementioned (1), wherein the aforementioned inorganic salt is a nitrate mixture consisting of 53% by mass of $KNO_3$ (potassium nitrate), 40% by mass of $NaNO_2$ (sodium nitrite) and 7% by mass of $NaNO_3$ (sodium nitrate).

(5) A (meth)acrolein or (meth)acrylic acid producing apparatus which is used in the production method described in any one of the aforementioned (1) to (4).

ADVANTAGE OF THE INVENTION

The method of the invention for producing (meth)acrylic acid and the like, characterized by the use of mica in the valve arranged on the piping for heat medium to be used in the oxidation reactor, is used in the production of (meth)acrolein and/or (meth)acrylic acid. By the production method of the invention, operational failure of the valve is excluded, and temperature control of the heat medium or handling of the heat medium becomes easy, so that stable and high quality production becomes possible.

DESCRIPTION OF THE REFERENCE NUMERALS AND SIGNS

The reference numerals 1b and 1c are reaction tubes, 2 is a reactor, 3a and 3b are circular conduits, 4a is a product discharging outlet, 4b is a raw material feeding inlet, 5a and 5b are tube plates, 6a and 6b are perforated baffles, 7 is a circulation pump, 8a is a heat medium supplying line, 8b is a heat medium discharging line, 9 is an intermediate tube plate, 10 is a heat shielding plate, 15 is a thermometer, 20 is a heat exchanger, and 21 is a control valve.

BEST MODE FOR CARRYING OUT THE INVENTION

The following describes the invention in detail.

The invention is a gas phase catalytic oxidation method for producing (meth)acrolein or (meth)acrylic acid or the like, characterized by the designing of a valve arranged on a piping which handles a heat medium to be used in a reactor that carries out gas phase catalytic oxidation.

According to this specification, acrylic acid from propylene or propane and methacrylic acid from isobutylene, when generally expressed, are expressed as (meth)acrylic acid.

The reactor type may be either a fluidized bed type or a fixed bed type, but a fixed bed type multi-tubular reactor is desirable.

Details of the production of (meth)acrolein and (meth)acrylic acid are described in the following.

[Reaction System]

Typical examples of the industrialized (meth)acrolein and (meth)acrylic acid production method include a one pass system, an unreacted propylene recycling system and an exhaust gas recycling system described in the following, and the reaction systems including these three systems are not restricted in the invention.

(1) One pass system:

This system is a method in which propylene, air and steam are mixed and supplied and converted mainly into (meth)acrolein and (meth)acrylic acid in the front stage reaction, and this outlet gas is supplied to the back stage reaction. In this case, a method in which air and steam necessary for carrying out the reaction in the back stage reaction are supplied to the last stage reaction, in addition to the front stage outlet gas, is also general.

(2) Unreacted propylene recycling system:

This system is a method in which a reaction product gas containing (meth)acrylic acid obtained by the back stage reaction is fed into a (meth)acrylic acid collecting device where (meth)acrylic acid is collected as an aqueous solution, and a part of the unreacted propylene is recycled by supplying a part of the collecting device-side exhaust gas containing unreacted propylene into the front stage reaction.

(3) Exhaust gas recycling system:

This system is a method in which a reaction product gas containing (meth)acrylic acid obtained by the back stage reaction is fed into an acrylic acid collecting device where (meth)acrylic acid is collected as an aqueous solution, whole volume of the exhaust gas of the collecting device side is oxidized by combustion to convert the unreacted propylene and the like contained therein mainly into carbon dioxide and water, and a part of the thus obtained combustion exhaust gas is added to the front stage reaction.

According to the invention, the "process gas" means gases concerned in the gas phase catalytic oxidation reaction, such as a substance to be oxidized as the raw material gas, a molecular oxygen-containing gas, an obtained product and the like.

[Raw Material Gas Composition]

A mixed gas of propylene, propane or isobutylene and/or (meth)acrolein as the raw material gas, a molecular oxygen-containing gas and steam is mainly fed into the multi-tubular reactor to be used in the gas phase catalytic oxidation.

According to the invention, concentration of propylene, propane or isobutylene in the mixed gas is from 6 to 10% by mole, and oxygen is from 1.5 to 2.5 moles and steam is from 0.8 to 5 moles per mole of propylene, propane or isobutylene. The introduced raw material gas is divided into respective reaction tubes, passes through the reaction tubes and undergoes the reaction in the presence of an included oxidation catalyst.

[Multi-Tubular Reactor]

The gas phase catalytic oxidation reaction which uses a fixed bad type multi-tubular reactor is a method broadly used in producing (meth)acrolein or (meth)acrylic acid from propylene or isobutylene, using molecular oxygen or a molecular oxygen-containing gas in the presence of a composite oxide catalyst.

According to the invention, the fixed bed type multi-tubular reactor is a generally industrially used one and has no particular limitation.

For example, this is a reactor consisting of a cylindrical reactor shell having a raw material supplying inlet and a product discharging outlet, two or more circular conduits arranged on the periphery of the cylindrical reactor shell for introducing or discharging a heat medium into or from the cylindrical reactor shell, a circulation device which mutually connects the two or more circular conduits, two or more reaction tubes which are contained by two or more tube plates of the reactor and include a catalyst, and two or more baffles for changing direction of the heat medium introduced into the reactor shell, all in the longitudinal direction of the reaction tubes.

In addition, the method of the invention for the production of (meth)acrolein or (meth)acrylic acid is a method for effecting gas phase catalytic oxidation of a substances to be oxidized with a molecular oxygen containing gas, and is a gas phase catalytic oxidation method which is carried out by filling an Mo-Bi-based catalyst and/or an Mo-V-based catalyst in the aforementioned reaction tubes.

Figure 1:
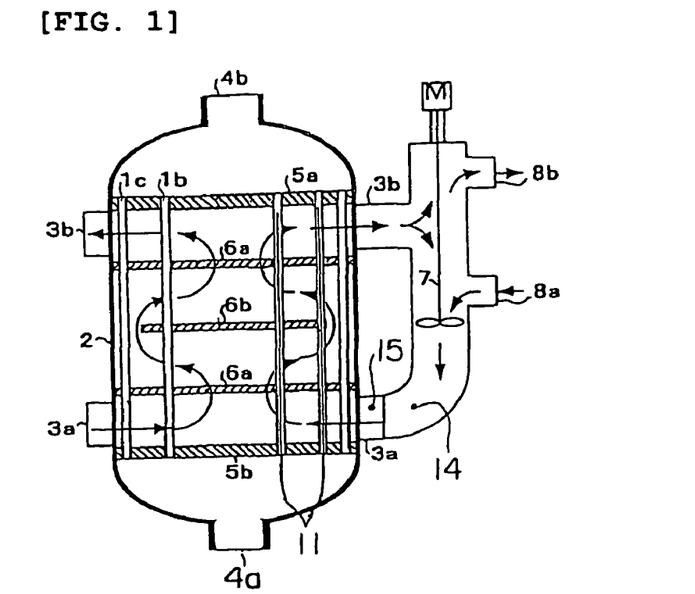
[FIG. 1] is an embodiment of the multi-tubular heat exchange type reactor to be used in the gas phase catalytic oxidation method of the invention.
Figure 2:
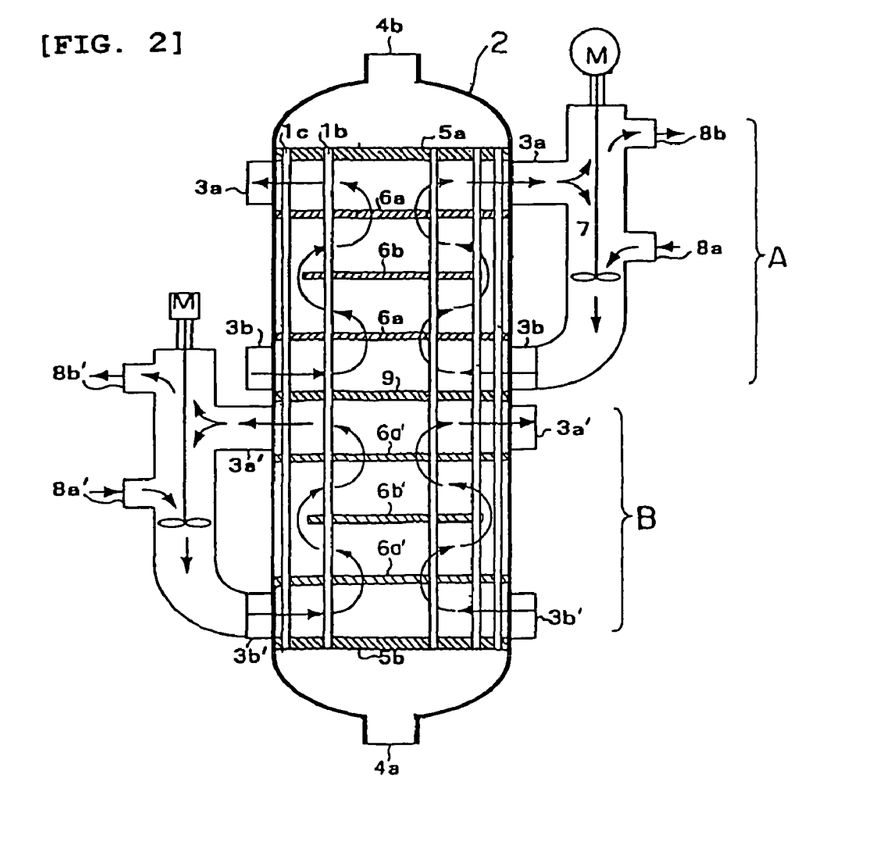
[FIG. 2] is another embodiment of the multi-tubular heat exchange type reactor to be used in the gas phase catalytic oxidation method of the invention.
Figure 5:
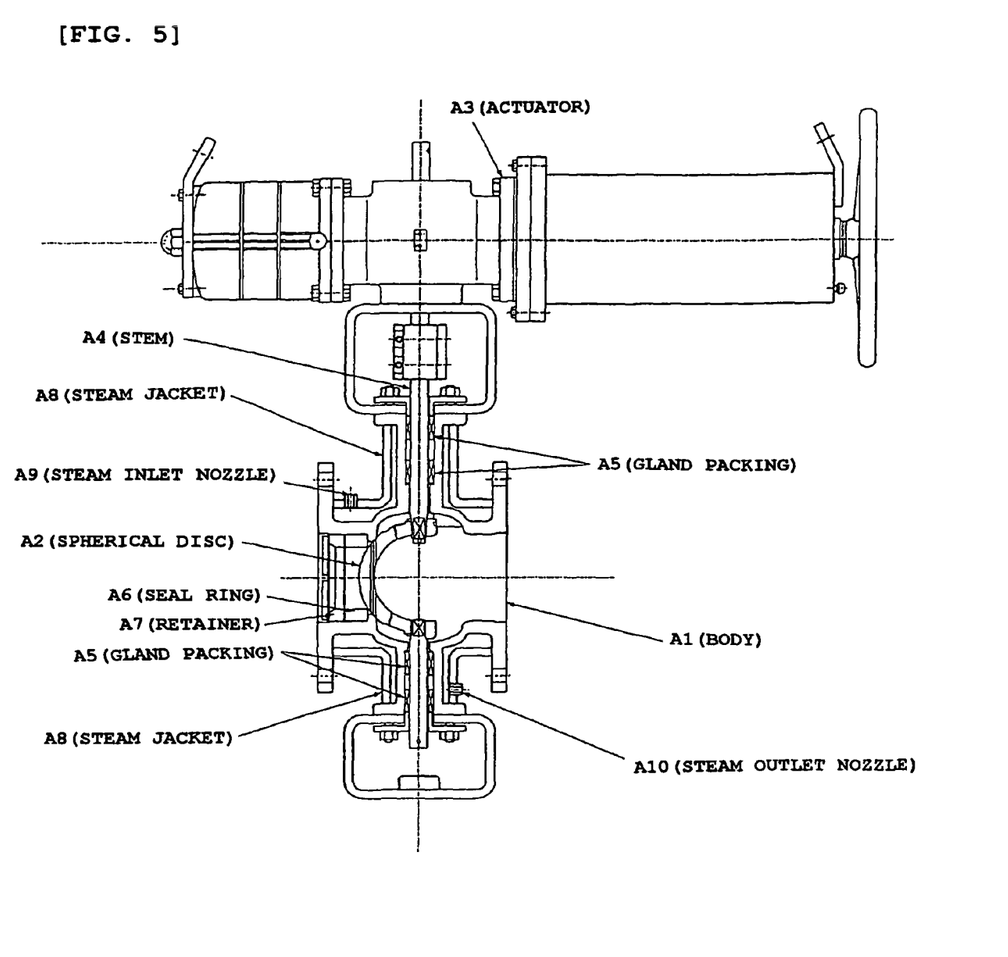
[FIG. 5] is a block diagram of an example of the regulating valve to be used in the heat medium circulation-temperature regulation system according to the invention.

The following describes an embodiment of the invention based on FIG. 1, FIG. 2 and FIG. 5.

FIG. 1 shows a multi-tubular heat exchange type reactor to be used in a typical embodiment of the gas phase catalytic oxidation method of the invention. In FIG. 1, reaction tubes 1b and 1c are fixed to tube plates 5a and 5b and arranged in a shell 2 of the multi-tubular reactor. An opening 4a or 4b which becomes a raw material supply port as an inlet of the raw material gas of the reaction or a product discharging port as an outlet of the product is arranged on the top part and bottom part of the shell 2, and one opening becomes the raw material supply port and the other the product discharging port depending on whether the process gas is down flow or up flow. Since flow direction of the heat medium inside of the reactor shell is shown in FIG. 1 by an arrow as ascending current, the opening 4b is the raw material supply port when the flow of the process gas and the heat medium is counter flow. However, flow direction of the process gas may be any direction. A circular conduit 3a for introducing the heat medium is arranged on the periphery of the reactor shell 2. The heat medium pressured by a circulation pump of the heat medium ascends inside of the reactor shell 2 from the circular conduit 3a and then is returned to the circulation pump 7 from a circular conduit 3b through its turning of flow direction due to the alternate arrangement of two or more of a perforated baffle 6a having an opening at around the central part of the reactor shell 2 and a perforated baffles 6b arranged in such a manner that it has an opening between a peripheral part and the reactor shell 2. A part of the heat medium which absorbed the heat of reaction is cooled by a heat exchanger (cf. FIG. 3) through a heat medium discharging line 8b arranged on the upper part of the circulation pump 7 and again introduced into the reactor from a heat medium supplying line 8a. Adjustment of the heat medium temperature is carried out by controlling temperature or flow rate of the circulated heat medium supplied from the heat medium supplying line 8a, by monitoring a thermometer 14 and in accordance with the temperature information.

Though it depends on the performance of the catalyst to be used, temperature control of the heat medium is carried out in such a manner that a difference in the heat medium temperature between the heat medium supplying line 8a and a heat medium discharging line 8b becomes from 1 to 10° C., preferably from 2 to 6° C.

In order to minimize circumferential distribution of the heat medium flow rate, it is desirable to arrange current plates (not shown in the drawing) on the inner shell plate parts of the circular conduits 3a and 3b. A porous plate, a plate having slits or the like is used as the current plate, and rectification is carried out by changing opening area or slit interval of the porous plate in such a manner that the heat medium inflows from the entire circumference at the same flow rate. Temperature in the circular conduit (3a, preferably 3b, too) can be monitored by arranging two or more of a thermometer 15.

The number of baffles to be arranged in the reactor shell 2 is not particularly limited, but it is desirable as usual to arrange 3 baffles (two 6a type and one 6b type). By the presence of these baffles, ascending flow of the heat medium is disturbed so that it turns into the transverse direction against the tube axis direction of the reaction tube, and the heat medium is concentrated into the central part of the reactor shell from its peripheral part, turns toward the peripheral part by turning the direction at the opening part of the baffle 6a and then reaches outer casing of the shell. The heat medium is concentrated into the central part by again turning the direction at the periphery of the baffle 6b, ascends the opening part of the baffle 6a, turns toward the periphery along the upper tube plate 5a of the reactor shell 2, and is recycled in the pump through the circular conduit 3b.

According to this embodiment, a thermometer 11 is inserted into at least one of the reaction tubes arranged in the reactor and transfers the signal to outside of the reactor, and temperature distribution in the reactor tube axis direction of the catalyst layer is recorded. One or two or more thermometers are inserted into the reaction tube, and from 5 to 20 points of temperatures are measured in the tube axis direction by one thermometer thereof.

The baffles to be used in the invention are not particularly limited, with the proviso that they have such a construction that it has an opening part around the central part of the reactor shell, the baffle has an opening between the peripheral part and outer casing of the shell, and the heat medium turns its direction at respective opening parts to prevent bypass flow of the heat medium and change its flow rate, and illustrative examples of their shape include segment type broken disc baffles, disc shape baffles and the like.

FIG. 2 shows a multi-tubular heat exchange type reactor to be used in another typical embodiment of the gas phase catalytic oxidation method of the invention. In FIG. 2, common member numbers are used for the members described in FIG. 1.

The reactor shown in FIG. 2 is an embodiment in which in the shell 2 or the reactor shown in FIG. 1 is divided with an intermediate tube plate 9, and a method which uses this reactor is also included in the method of the invention. Different heat media are circulated and controlled at different temperatures in the divided spaces. In FIG. 2, flow direction of the heat medium is ascending current according to the arrow. The raw material gas may be supplied from either the opening 4a or opening 4b, but it is desirable that it becomes counter flow against the flow of heat medium. In that case, the opening 4b is the raw material supply port, and the raw material gas supplied from the opening 4b successively undergoes the reaction in the reaction tubes of the reactor.

Heat media having different temperature are present in the upper and lower areas (A and B) of the reactor divided with the intermediate tube plate 9 according to the multi-tubular reactor shown in FIG. 2. Inside of each reaction tube is divided into 1) a case in which the same catalyst is evenly filled and the reaction is carried out by changing temperature at the raw material gas inlet and outlet of the reaction tube, 2) a case in which a catalyst is filled in the raw material gas inlet, but in order to rapidly cool the reaction product, the catalyst is not filled in the outlet part to form an empty tube or an inert substance having no reaction activity is filled therein, and 3) a case in which different catalysts are filled in the raw material gas inlet part and outlet part, but in order to rapidly cool the reaction product, the catalyst is not filled between them to form an empty tube or an inert substance having no reaction activity is filled therein.

For example, propylene, propane or isobutylene is supplied as a mixed gas with a molecular oxygen-containing gas from the opening 4b as a raw material feeding inlet into the multi-tubular reactor shown in FIG. 2 to be used in the invention and firstly converted into (meth)acrolein at the first step for the front stage reaction (represents area A of the reaction tube, and is referred sometimes to as "front stage part"), and then (meth) acrylic acid is produced at the second step for the back stage reaction (represents area B of the reaction tube, and is referred sometimes to as "back stage part") by oxidizing the (meth)acrolein. Different catalysts are filled in the first step part and the second step part of the reaction tube, and the reactions are carried out under optimum conditions by controlling at respectively different temperatures. It is desirable that an inert substance which is not concerned in the reaction is filled in a part where the intermediate tube plate 9 is present between the front stage part and the back stage part of the reaction tube.

When the difference in temperature between the front stage part and the back stage part exceeds 100° C., it is desirable to use two or more heat shielding plates at a position of about 10 cm upside or downside of the intermediate tube plate 9 in order to prevent thermal transfer.

Though flow direction of the heat medium inside of the reactor shell is described as an ascending flow by an arrow in FIG. 1 and FIG. 2, the reverse direction can also be possible in the invention. In deciding direction of circulating flow of the heat medium, it is necessary to avoid a phenomenon in which a gas which may be present in the upper terminals of the reactor shell 2 and circulation pump 7, illustratively nitrogen or the like inert gas, is dragged in the flow of heat medium. In case that the heat medium is ascending flow (FIG. 1), a cavitation phenomenon is found inside the circulation pump 7 when a gas is dragged in the upper part of the circulation pump, causing damage of the pump in the worst case. When the heat medium is descending flow, a dragging phenomenon of a gas occurs also in the upper part of the reactor shell, so that a stagnant part of a gas phase is formed in the upper part of the shell, and the upper part of the reaction tube of that part cannot be cooled by the heat medium.

In order to prevent the gas stagnation, it is essential to replace the gas in the gas layer with the heat medium by arranging a degassing line, and for this purpose, pressure increase in the shell is devised by increasing heat medium pressure of the heat medium supplying line 8a and arranging the heat medium discharging line 8b at a position as upper as possible. It is desirable to arrange the heat medium discharging line on at least upper side of the tube plate 5a.

When the multi-tubular reactor shown in FIG. 1 is used as a multi-tubular reactor for oxidizing propylene, propane or isobutylene with a molecular oxygen-containing gas, and the process gas is descending flow, that is, when the raw material gas is supplied from 4b and the product is discharged from 4a, (meth)acrolein as the product of interest has a high concentration and is heated by the heat of reaction at around the product discharging port 4a of the reactor so that the process gas temperature also becomes high. Accordingly, it is desirable in that case to arrange a heat exchanger at a position in or after 4a of the reactor of FIG. 1, so that the process gas is sufficiently cooled and (meth)acrolein does not generate auto-oxidation reaction.

Also, when the multi-tubular reactor shown in FIG. 2 is employed, and the process gas is descending flow, that is, when the raw material gas is supplied from 4b and the product is discharged from 4a, (meth)acrolein as the product of interest has a high concentration and is heated by the heat of reaction at around the intermediate tube plate 9 as the reaction completion point of the first stage (area A of the reaction tube), so that the process gas temperature also becomes high. When a catalyst is filled only in the first stage (area A of the reaction tube: 5a-6a-6b-6a-9), the reaction is not actively advanced in the second stages of reaction tubes 1b and 1c (area B of the reaction tubes: between 9 and 5b), so that the process gas is cooled by the heat medium flowing in the shell-side channel and (meth)acrolein does not generate auto-oxidation reaction. In that case, the catalyst is not filled in the area B of the reaction tubes 1b and 1c (between 9 and 5b) to form an empty tube, or a solid having no reaction activity is filled therein. The latter is desirable for improving characteristics of thermal transfer.

When different catalysts are filled in the first stage (area A of the reaction tube: 5a-6a-6b-6a-9) and the second stage (area B of the reaction tube: 9-6a'-6b'-6a'-5b) of the multi-tubular reactor shown in FIG. 2, and (meth)acrolein is obtained from propylene, propane or isobutylene at the first stage and (meth)acrylic acid is obtained at the second stage, catalyst layer temperature of the first stage becomes high in comparison with the catalyst layer temperature of the second stage. Illustratively, since the temperature becomes high at around the reaction completion point of the first stage (6a to 9) and at around the reaction initiation point of the second stage (9 to 6a'), it is desirable that the reaction is not carried out at this moiety, so that the process gas is cooled by the heat medium flowing in the shell-side channel and (meth)acrolein does not generate auto-oxidation reaction. In that case, a part where the catalyst is not filled is arranged around the intermediate tube plate 9 (among 6a to 9 to 6a' of the reaction tubes 1b and 1c) to form an empty tube, or a solid having no reaction activity is filled therein. The latter is desirable for improving characteristics of thermal transfer.

[Reaction Tube Diameter]

Though it depends on the quantity of heat of reaction and catalyst particle size in the reaction tube, the reaction tube inner diameter of the multi-tubular reactor is generally from 10 to 50 mm, preferably from 20 to 30 mm. When the reaction tube inner diameter is too small, amount of the catalyst to be filled is reduced so that the number of reaction tubes required for supplying necessary amount of catalyst into the reactor is increased, thus showing a tendency of worsening reactor production cost and the like economical efficiencies. On the other hand, when the reaction tube inner diameter is too large, it causes a tendency of worsening heat removing efficiency.

[Heat Medium and Heat Transfer Coefficient]

As the heat medium to be supplied into shell side of the reactor, a mixture of nitrates (to be referred sometimes to as "niter" hereinafter), a phenyl ether organic liquid or the like is used. According to the invention, a mixture of nitrates is regarded as a particularly desirable object of the heat medium.

An example of the composition of niter is 53% by mass of $KNO_3$ (potassium nitrate), 40% by mass of $NaNO_2$ (sodium nitrite) and 7% by mass of $NaNO_3$ (sodium nitrate). When this is made into a different weight composition, melting point of the mixture changes. Acceptable range of the composition of niter depends on the temperature condition for its use.

It is desirable to use industrial products having a purity of 95% by mass or more as $KNO_3$ (potassium nitrate), $NaNO_2$ (sodium nitrite) and $NaNO_3$ (sodium nitrate). When the purity is less than 95% by mass, it causes a tendency of showing a large slippage from the melting point designed as the mixture.

The heat of reaction in the reaction tube is removed by the flow of the heat medium. The heat medium introduced into inside of the reactor shell from a circular conduit for heat medium introduction (e.g., 3a of FIG. 1) has a region where it flows from peripheral part into the central part of the reactor and a region where it reverses its flow direction at the central part, and the heat removing effect greatly varies in these regions. When flow direction of the heat medium and tube axis direction of the reaction tube are at right angles to each other, the heat transfer coefficient is from 1,000 to 2,000 $W/m^{2\circ}$ C. When flow direction of the heat medium and tube axis direction of the reaction tube are not at right angles to each other, the heat transfer coefficient depends on the flow rate and flow direction but is generally from 100 to 300 $W/m^{2\circ}$ C.

Since the heat transfer coefficient of catalyst layer inside the reaction tube depends on the flow rate of the raw material gas and is generally about 100 $W/m^{2\circ}$ C., rate-determining stage of the heat transfer is the heat transfer in the gas phase in the tube. When flow of the heat medium is at right angles to the reaction tube axis, heat transfer resistance outside the tube is approximately from 1/10 to 1/20 of that of the tube gas side, so that influence of the change in flow rate of the heat medium upon the overall heat transfer resistance is small. However, when flow of the heat medium is parallel to the reaction tube axis, the heat transfer coefficient is almost the same inside and outside of the reaction tube, so that the heat transfer efficiency by heat removal is greatly influenced by the fluid condition of the heat medium. For example, when heat transfer resistance of the heat medium outside the tube is 100 $W/m^{2\circ}$ C., the overall heat transfer coefficient becomes half of that, and half of the change in heat transfer resistance outside the tube exerts influence upon the overall heat transfer coefficient.

[Catalyst]

As the catalyst to be used in the production of (meth) acrolein or (meth)acrylic acid by gas phase catalytic oxidation reaction, those which are used in the front stage reaction of from olefin to unsaturated aldehyde or unsaturated acid and those which are used in the back stage reaction of from unsaturated aldehyde to unsaturated acid are present, and they can be applied to each of the reactions according to the invention.

Compounds represented by the following compositional formula (I) can be exemplified as the Mo-Bi-based composite oxide catalyst to be used in the front stage reaction.

Compositional formula (I): $Mo_aW_bBi_cFe_dA_eB_fC_gD_hE_iO_x$

In the compositional formula (I), Mo is molybdenum, W is tungsten, Bi is bismuth, Fe is iron, A is at least one element selected from nickel and cobalt, B is at least one element selected from sodium, potassium, rubidium, cesium and thallium, C is at least one element selected from alkaline earth metals, D is at least one element selected from phosphorus, tellurium, antimony, tin, cerium, lead, niobium, manganese, arsenic, boron and zinc, E is at least one element selected from silicon, aluminum, titanium and zirconium, and O is oxygen. The signs a, b, c, d, e, f, g, h, i and x respectively represent atomic ratios of Mo, W, Bi, Fe, A, B, C, D, E and O, and when a is 12, b is from 0 to 10, c is from 0 to 10 (preferably from 0.1 to 10), d is from 0 to 10 (preferably from 0.1 to 10), e is from 0 to 15, f is from 0 to 10 (preferably from 0.001 to 10), g is from 0 to 10, h is from 0 to 4, i is from 0 to 30, and x is a value which is determined by the oxidized state of each element.

Compounds represented by the following compositional formula (II) can be exemplified as the Mo-V-based composite oxide catalyst to be used in the back stage reaction.

Compositional Formula (II): $Mo_aV_bW_cCu_dX_eY_fO_g$

In the compositional formula (II), Mo is molybdenum, V is vanadium, W is tungsten, Cu is copper, X is at least one element selected from Mg, Ca, Sr and Ba, Y is at least one element selected from Ti, Zr, Ce, Cr, Mn, Fe, Co, Ni, Zn, Nb, Sn, Sb, Pb and Bi, and O is oxygen. The signs a, b, c, d, e, f and g respectively represent atomic ratios of Mo, V, W, Cu, X, Y and O, and when a is 12, b is from 0 to 14, c is from 0 to 12, d is from 0 to 6, e is from 0 to 3, f is from 0 to 3, and g is a value which is determined by the oxidized state of each element.

The aforementioned catalysts are produced, for example, by the methods disclosed in JP-A-63-54942, JP-B-6-13096, JP-B-6-38918 and the like.

The aforementioned catalysts may be formed catalysts formed by extrusion molding or tablet compression, or carried catalysts in which a composite oxide consisting of catalyst components is supported on an inert carrier such as silicon carbide, alumina, zirconium oxide, titanium oxide or the like.

Shape of the catalyst is not particularly limited, and its examples include spherical, columnar, cylindrical, star-shaped, ring-shaped, amorphous and the like.

[Diluent]

The aforementioned catalyst can also be used by mixing with an inert substance as a diluent.

The inert substance is not particularly limited, with the proviso that it is a substance which is stable under the aforementioned reaction conditions and has no reactivity with the raw material substance and product, and illustratively, alumina, silicon carbide, silica, zirconia oxide, titanium oxide and the like substances used as the carrier of catalyst.

In addition, its shape is not particularly limited similar to the case of catalyst, and it may be in any shape such as spherical, columnar, cylindrical, star-shaped, ring-shaped, small piece-like, net-like, amorphous and the like. The size is determined by taking the reaction tube diameter and pressure loss into consideration.

<Mixing of Catalyst with Diluent>

Using amount of the inert substance as a diluent is determined such that the catalyst activity of interest can be obtained. For example, using amount of the inert substance may be increased in a filling layer around the raw material gas inlet or the like where the catalytic activity is lowered for the purpose of controlling exothermic heat in the reaction tube, or using amount of the inert substance may be reduced in a filling layer around the reaction gas outlet or the like where the catalytic activity is increased. Alternatively, the catalyst and diluent may be mixed at a predetermined ratio and filled in the reaction tube in one layer.

In an applicable method in the case of two layer filling, an inert substance particle using ratio of from 0.3 to 0.7 is used as a catalyst having high inert substance particle ratio in the raw material gas inlet part of the reaction tube, and an inert substance particle using ratio of from 0 to 0.5 is used by filling a catalyst having such a low ratio or without dilution in the outlet side of the reaction tube.

The number of catalyst layers formed in the tube axis direction of the fixed bed multi-tubular reactor is not particularly limited, but is generally from 1 to 10 When the number of catalyst layers is too many, considerable labor is required for the catalyst filling work. The length of each catalyst layer may be determined based on the catalyst species, the number of catalyst layers, reaction conditions and the like.

[Method for Adjusting Temperature of Heat Medium]

According to the invention, the heat medium temperature adjusting method is not particularly limited.

Figure 3:
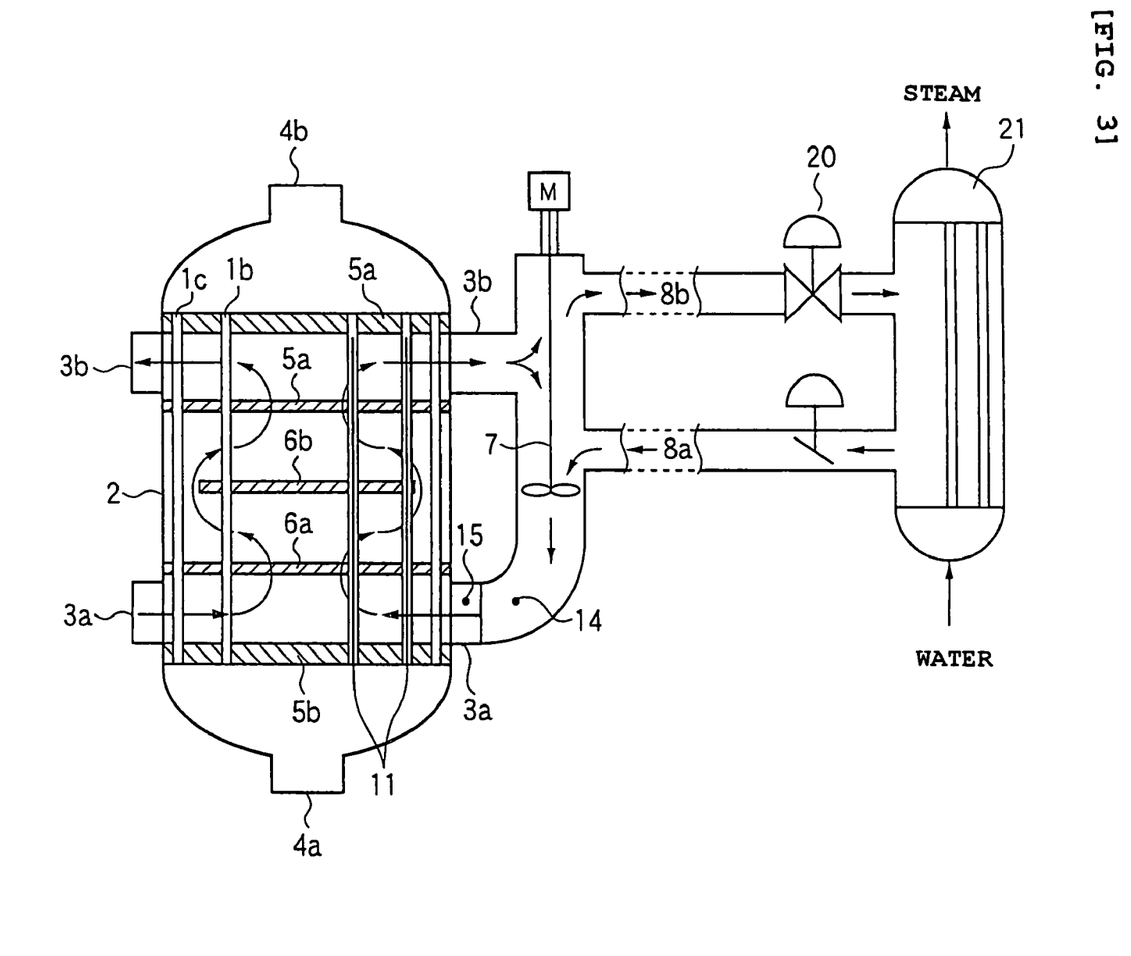
[FIG. 3] is an embodiment of a system of the multi-tubular heat exchange type reactor and heat exchanger to be used in the invention.
Figure 4:
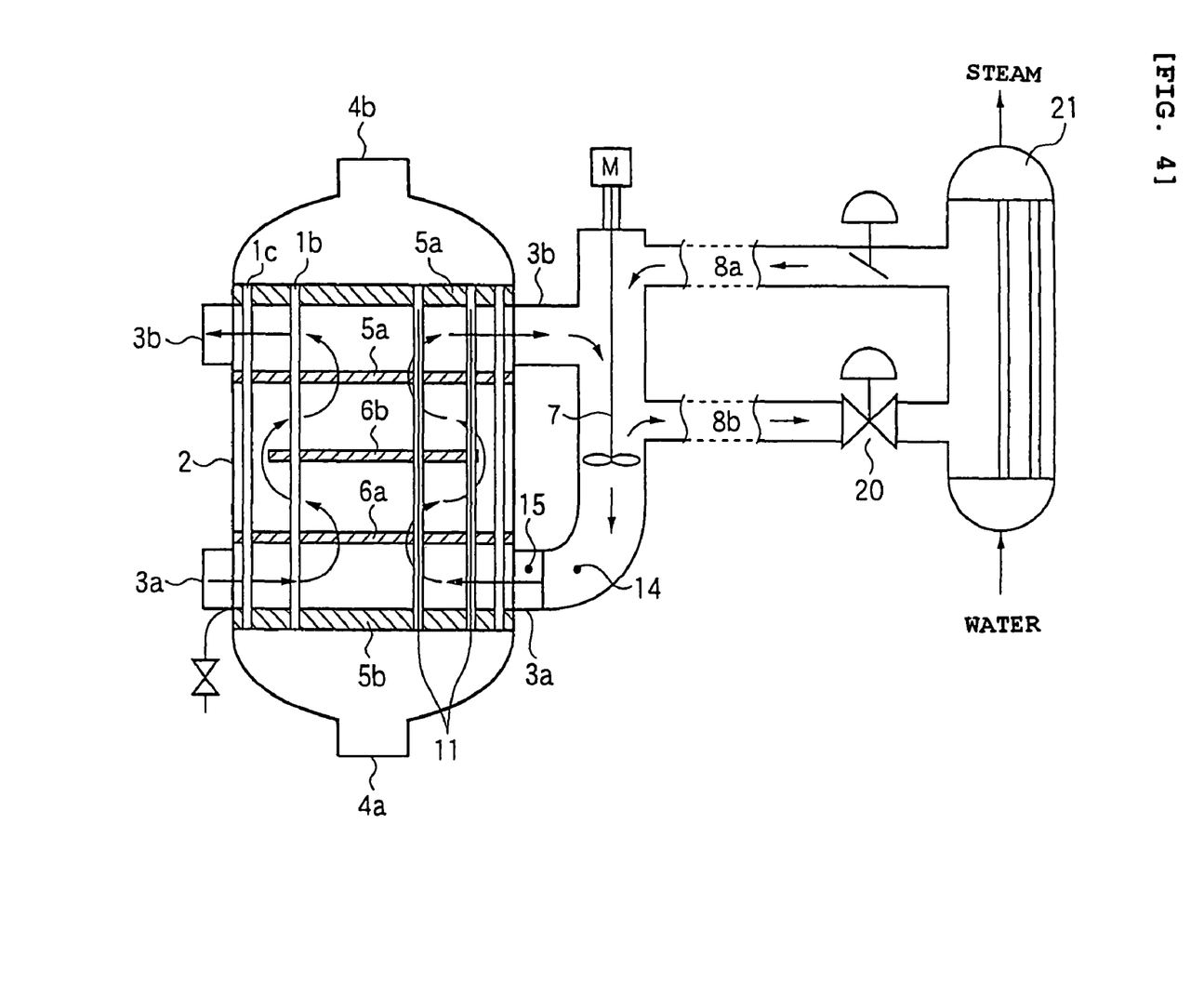
[FIG. 4] is another embodiment of a system of the multi-tubular heat exchange type reactor and heat exchanger to be used in the invention.

For example, according to an example of the system of reactor and heat exchanger shown in FIG. 3, the heat medium temperature can be adjusted by cooling, with a heat exchanger 20 of FIG. 3, a part or all of the heat medium took out from the upper side of a circulation pump 7 of the reactor by a heat medium discharging line 8b, and circulating the cooled heat medium into the reactor by returning it to the system of reactor through a heat medium supplying line 8a. Amount of the heat medium to be took out is adjusted to a suitable volume by a control valve 21. As another embodiment, as shown in FIG. 4, the heat medium heat-exchanged by arranging the heat medium discharging line 8b in the lower side of the circulation pump 7 of the reactor may be circulated by returning it to the system of reactor through the heat medium supply line 8a arranged in the upper side of the circulation pump 7. Selection of these embodiments is carried out in response to the apparatus conditions, raw material conditions and the like.

When heat medium temperature becomes high due to absorption of heat of reaction by the heat medium, the temperature to be increased is generally from 1 to 10° C., preferably from 2 to 6° C., in order to avoid formation of hot spot (active spot) from the viewpoint of catalyst protection.

Type of the heat exchanger is not particularly limited. Its illustrative examples include a vertical fixed tube plate type, a horizontal fixed tube plate type, a U tube type, a double tube type, a spiral type, an angular block type and the like.

Though not particularly limited, examples of the material include carbon steel, stainless steels and the like which may be selected in view of heat resistance, corrosion resistance, economic efficiency and the like.

[Control Valve to be Arranged on the Device or Piping of Heat Medium]

Since the temperature difference is very small as described in the foregoing (generally from 1 to 10° C.), precise control is required for a valve which controls amount of the warmed heat medium to be supplied to the heat exchanger. On the other hand, since the heat medium consists of high melting point substances, it immediately solidifies when cooled by outgoing radiation or heat transfer so that operation of the valve becomes unstable or non-operable.

According to the invention, gland of the valve does not use a graphite-based material but it uses a mica-based material. When a graphite-based material is used, niter penetrates into the gland which therefore becomes operation-defective.

Also, according to the invention, it is desirable to employ a jacket structure by which gland part of the valve is heated. By doing this, solidification of the heat medium is prevented, and smooth operation of the valve is ensured over a prolonged period of time, thus rendering possible the control precisely corresponding to small changes in the temperature and flow rate.

In addition, a device having sufficiently large power is employed in the actuator of the valve. The sufficiently large power means a driving force having a [sliding frictional force between the body part and a stem interfitting thereto]/[actuator maximum generation force] of 0.2 or less in the state of not flowing a fluid. More preferably, it is 0.15 or less. A value of larger than 0.2 is not sufficient for carrying out precise control. This is because the valve is required to have a sufficiently large driving force.

Also in the case of the valve, it is necessary to carry out operational check (including a verification of whether it precisely acts by 1% intervals) prior to the commencement of operation, by discharging the heat medium (niter) after shutdown of the equipment (e.g., yearly periodic maintenance or the like), always removing it when the equipment was cooled, and checking the inside thereof.

Particularly in the case of an equipment system in which only one heat medium temperature-controlling valve is equipped in its heat medium circulating and temperature controlling system, the temperature control becomes impossible when poor operation occurs, so that strict enforcement of the aforementioned maintenance and checking works is considerably effective.

A typical embodiment of the aforementioned control valve characteristic of the heat medium circulating and temperature controlling system of the equipment to be applied to the gas phase catalytic oxidation method of the invention is further described based on FIG. 5.

FIG. 5 is a block diagram of an example of the control valve to be used in the heat medium circulating and temperature controlling system according to the invention. A spherical disc ball valve is employed in FIG. 5 as a type of the control valve, but regarding the type of the control valve, it may be a valve other than the spherical disc ball valve of FIG. 5, such as a ball valve, globe valve, a gate valve or a butterfly valve.

In FIG. 5, A1 (body) is a valve main body which may be a flanged typed (the embodiment of FIG. 5) or an insertion type without a flange. In addition, carbon steel, stainless steels and the like are generally used as the material, but not limited thereto, and it may be selected in view of heat resistance, corrosion resistance, economic efficiency and the like.

A2 (spherical disc) carries out an action to control differential pressure of fluid by rotating about 90 degree inside the valve main body. In the case of the aforementioned other type of control valve, the spherical disc A2 may have a form of sliding to the vertical direction against current of the fluid.

In order to carry out remote control of the control valve, A3 (actuator) receives a signal of electricity or a gas (air, nitrogen or the like) from a control panel in the control room, and converts the signal into a force of direction necessary for driving the valve. Its type may be a cylinder type or diaphragm type. The driving force converted by the actuator is transferred to the spherical disc A2 by A4 (stem), thereby achieving function of the valve. Depending on the type of the valve, the stem A4 may either rotates against the axis direction or slides toward the axis direction. A5 (gland packing) is inserted into sealing of the stem A4 and body A1, and according to the invention, a graphite-based material generally used as a heat resisting material is not used but a mica-based material must be used as its material. When it is a graphite-based material, the material undergoes corrosion by niter so that it is apt to generate sticking of the stem with a gland part, but this is prevented by the use of a mica-based material. The mica-based material to be used in the invention is a generally defined mica-based material, namely an alkali metal-containing aluminosilicate, and based on the chemical structure, it includes muscovite, lepidolite, paragonite, vanadinite, sericite and the like muscovites, biotite, phlogopite, lepidomelane, zinnwaldite and the like biotites, slauconite, celadonite and the like, but when used as an apparatus member, their discrimination is not required in most cases because they have similar characteristics so that they are simply called mica.

On the other hand, the space between the spherical disc A2 and body A1 is sealed by fixing A6 (seal ring) with A7 (retainer). In order to prevent poor operation due to aggregation of niter, A8 (steam jacket) is attached to the body A1 and gland part. It is desirable to make the steam jacket into a full jacket, but it may be a semi-jacket when attachment of the jacket is difficult due to structure of the valve.

In addition, taking distortion by thermal expansion into consideration, the same material as that of the body is employed. A high pressure steam having a saturation temperature of higher than the melting point of the heat medium is supplied from A9 (steam inlet nozzle) into this steam jacket, and condense water is recovered from A10 (steam outlet nozzle).

EXAMPLES

In order to illustratively describe the invention, it is described in detail with reference to Examples and Comparative Examples, though not limited thereto.

Example 1

Catalyst

After dissolving 94 parts by weight of antimony paramolybdate in 400 parts by weight of pure water under heating, 7.2 parts by weight of ferric nitrate, 25 parts by weight of cobalt nitrate and 38 parts by weight of nickel nitrate were dissolved in 60 parts by weight of pure water under heating. These solutions were mixed by sufficient stirring.

Next, 0.85 part by weight of borax and 0.36 part by weight of potassium nitrate were dissolved in 40 parts by weight of pure water under heating and added to the aforementioned slurry. Next, 64 parts by weight of granular silica was added thereto and stirred. Next, 58 parts by weight of bismuth subcarbonate compounded in advance with 0.8% by weight of Mg was added thereto and mixed with stirring, this slurry was dried under heating and then treated with heating at 300° C. for 1 hour in an atmosphere of air, and the thus obtained granular solid was subjected to tablet compression using a molding machine to form a tablet of 5 mm in diameter and 4 mm in height and then subjected to 4 hours of baking at 500° C. to obtain a catalyst.

The thus obtained catalyst was a catalyst powder of Mo-Bi-based composite oxide having a compositional ratio of Mo(12)Bi(5)Ni(3)Co(2)Fe(0.4)Na(0.2)Mg(0.4)B(0.2)K(0.1) Si(24)O(x) (the composition x of oxygen is a value determine by the oxidized state of each metal).

In this example, a multi-tubular reactor similar to the one shown in FIG. 1 was used.

Illustratively, a multi-tubular reactor consisting of a reactor shell (4,500 mm in inner diameter) having 10,000 stainless steel-made reaction tubes, each reaction tube having a length of 3.5 m and an inner diameter of 27 mm, was used. The reaction tubes are not arranged in the central circular opening part region of the perforated disc shape baffle 6a having an opening part near the central part of the reactor shell. The baffles are arranged in such a manner that the perforated disc shape baffle 6a having an opening part near the central part of the reactor shell and the perforated disc shape baffle 6b positioned to have an opening part between the peripheral part and the reactor shell become the same intervals of 6a-6b-6a in that order, and the opening ratio of each baffle is 18%.

A molten salt mixture of nitrates (niter) was used as the heat medium and circulated by supplying from a lower part of the reactor and discharging from an upper part of the reactor.

A part of this heat medium was discharged from one of the heat medium supplying line 8b, cooled by a heat exchanger having a structure shown in FIG. 5, and then returned to the other heat medium supplying line 8a (cf. FIG. 3). The discharged amount was adjusted by the control valve (21 of FIG. 3, details are shown in FIG. 5) equipped in a heat medium supplying line system (8b-heat exchanger-8a). Temperature of the heat medium to be supplied into the reactor was adjusted by this, and this temperature was measured by the thermometer (15 of FIG. 1). The control valve 21 is a valve in which a packing of mica (a commercially available mica) is used in the gland, and which is covered, including the gland, with a steam jacket and set in such a manner that it has a [sliding frictional force between the body part and a stem interfitting thereto]/[actuator maximum generation force] value of 0.2 in the state of not flowing a fluid.

In starting the operation, operating state of the valve was verified, and its control at 1% intervals was confirmed.

As the catalyst to be filled in each reaction tube, the aforementioned front stage catalyst was used after adjusting its catalytic activity by mixing it with silica-made balls having a diameter of 5 mm and not having catalytic activity, and filled from the reaction tube inlet such that the ratio of catalytic activity became 0.5, 0.7 and 1.

The raw material gas was supplied from the upper part of the reactor in the counter flow system with the heat medium, and a raw material gas consisting of 9% by mol concentration of propylene, 1.9% by mol concentration of molecular oxygen, 9% by mol concentration of water and 80.1% by mol concentration of nitrogen was supplied at a rate of 12,300 Nm$^3$/h under a gauge pressure of 75 kPa (kilopascal). Temperature distribution in the reaction tube was measured by inserting a thermometer having 10 measuring points in the tube axis direction.

When this was operated for 1 week by setting the heat medium inlet temperature to 335° C., the first catalyst layer showed the most high reaction peak temperature of 395° C., propylene conversion ratio was 97%, and the total yield of acrolein and acrylic acid was 92%. As the reaction temperature, temperature of the niter to be supplied into the reactor was used. Temperature difference between the inlet and outlet of niter was 3° C.

The niter was supplied into the heat exchanger via the aforementioned control valve for adjusting the temperature, cooled and then returned to the reaction system from 8a.

The control valve for temperature adjustment continued its safe operation for 1 year.

Comparative Example 1

The operation was carried out by the same method of Example 1 using the control valve used in Example 1 having the same shape and operational mechanism, except that the material of gland packing was graphite carbon, and the [sliding frictional force between the body part and a stem interfitting thereto]/[actuator maximum generation force] value was changed to 0.4 in the state of not flowing a fluid. An operational failure occurred 2 months after commencement of the operation, and the operation was stopped because of a difficulty in adjusting temperature of the niter.

Example 2

The operation was carried out in the same manner as in Example 1, except that the valve was changed so that the sliding frictional force by the gland/actuator maximum generation became 0.06 in the state of not flowing a fluid. The same mica of Example 1 was used in the sealing material of the control valve.

Since operation of this control valve was markedly smooth, temperature control was also carried out accurately, so that it was able to carryout the continuous operation for 1 year.

While the invention has been described in detail and with reference to specific embodiments thereof, it will be apparent to one skilled in the art that various changes and modifications can be made therein without departing from the spirit and scope thereof.

This application is based on a Japanese patent application filed on May 19, 2004 (Japanese Patent Application No. 2004-148875), the entire contents thereof being hereby incorporated by reference.

The invention claimed is:

1. A method for producing (meth)acrolein or (meth)acrylic acid by carrying out gas phase catalytic oxidation reaction of propane, propylene, isobutylene or (meth)acrolein with an oxygen-containing gas using an inorganic salt as a reaction temperature adjusting heat medium, characterized in that a material of a gland packing member which seals a body part of a regulating valve arranged on a heat medium feeder and controls supply and circulation velocity of the heat medium and a rotation axis that interfits to said body part, in such a manner that the gland packing member and the body part of the regulating valve can perform sliding, is a mica-based material, wherein the gland part of said regulating valve includes a heating jacket, and wherein an actuator of said regulating valve has a ratio (sliding frictional force between the body part and a stem interfitting thereto)/(an actuator maximum generation force) of 0.2 or less in the state of not flowing a fluid.

2. The method for producing (meth)acrolein or (meth)acrylic acid according to claim 1, wherein said inorganic salt is a nitrate mixture consisting of 53% by mass of $KNO_3$ (potassium nitrate), 40% by mass of $NaNO_2$ (sodium nitrite) and 7% by mass of $NaNO_3$ (sodium nitrate).

3. A (meth)acrolein or (meth)acrylic acid producing apparatus characterized in that it is used in the production method described in claim 1.

4. A process for producing (meth)acrolein or (meth)acrylic acid, comprising:

carrying out a gas phase catalytic oxidation of a reaction mixture comprising one or more of propane, propylene, isobutylene and (meth)acrolein, and an oxygen-containing gas at a reaction temperature;

controlling the reaction temperature of the reaction mixture by adjusting at least one of the amount and the circulation velocity of a heat medium, wherein the heat medium is an inorganic salt;

wherein adjusting at least one of the amount of the heat medium and the circulation velocity of the heat medium is carried out by adjusting a regulating valve, wherein the regulating valve comprises (i) a valve body, (ii) a stem inserted into the valve body and capable of rotation through a longitudinal axis of the stem, and (iii) a gland in contact with the stem and the valve body, wherein the gland seals the interior of the valve body between the stem and the valve body, wherein the gland and the valve body slide against one another during the adjusting, wherein at least one of the gland and the stem is a mica-based material, wherein the regulating valve further comprises a heating jacket surrounding the valve body, and wherein the ratio (sliding friction force between the valve body and the stem)/(an actuator maximum generation force) is 0.2 or less when measured in the absence of a flowing fluid.

5. The process of claim 4, wherein at least one of the gland and the stem has a surface consisting of mica.

6. The process of claim 4, wherein both the gland and the stem are mica.

7. The method of claim 4, wherein the heat medium is a mixture consisting of 53% by mass of $KNO_3$, 40% by mass of $NaNO_2$ and 7% by mass of $NaNO_3$.

8. The method of claim 1, wherein the regulating valve is a spherical disc ball valve.

9. The method of claim 4, wherein the regulating valve is a spherical disc ball valve.

10. The method of claim 1, wherein the ratio (the sliding frictional force between the body part and the stem interfitting thereto)/(an actuator maximum generation force) is from 0.06 to 0.2.

11. The method of claim 4, wherein the ratio (sliding friction force between the valve body and the stem)/(an actuator maximum generation force) is from 0.06 to 0.2.

* * * * *